United States Patent [19]

Hara et al.

[11] Patent Number: 4,600,306
[45] Date of Patent: Jul. 15, 1986

[54] APPARATUS FOR MEASURING THE LUMINOUS LIFETIME OF A SAMPLE

[75] Inventors: Kiyoaki Hara; Issei Yokoyama, both of Kyoto, Japan

[73] Assignee: Horiba, Ltd., Kyoto, Japan

[21] Appl. No.: 539,680

[22] Filed: Oct. 6, 1983

[30] Foreign Application Priority Data

Oct. 19, 1982 [JP] Japan .................. 57-183244

[51] Int. Cl.⁴ ............................ G01N 21/64
[52] U.S. Cl. .................... 356/317; 250/461.1
[58] Field of Search .............. 356/317, 318, 417; 250/365, 461.1

[56] References Cited

U.S. PATENT DOCUMENTS 3,918,812 11/1975 Holm .................. 250/365

FOREIGN PATENT DOCUMENTS 57-137843 8/1982 Japan .

OTHER PUBLICATIONS

"Nanosecond Time–Resolved Spectroscopy with a Pulsed Tunable Dye Laser and Single Photon Time Correlation," Meltzer et al., *Applied Optics*, vol. 16, No. 5, p. 1432, 5/77.
"Lifetime Determinations and Their Errors Using Pulsed Dye Lasers," Atkinson, *J. Phys. E., Sci. Instrum.*, vol. 10, No. 5, p. 482, May 1977.
"Developments in Photophysical Instrumentation," West et al., American Laboratory, vol. 8, No. 11, p. 77, Nov. 1976.
"Photon Counting System for Subnanosecond Fluorescence Lifetime Measurement," Leskovar et al., *Rev. Sci. Instrum.*, vol. 47, No. 9, p. 1113, Sep. 1976.
"A 10 ns Multichannel Photon Counter," Lawton et al., *J. Phys. E. Sci. Instrum.* vol. 9, 1976.
"High Speed Spectroscopic Measurement of Very Weak Radiation with Multichannel Coincidence Technique," Minami et al., *Japanese J. of Appl. Phys.*, vol. 14, p. 39, 1975.
"Analyzing Fluorescence Decay," Measures et al., *Laser Focus*, Nov. 1974, p. 49.

Primary Examiner—F. L. Evans
Assistant Examiner—Joel L. Harringa
Attorney, Agent, or Firm—Wenderoth, Lind & Ponack

[57] ABSTRACT

A pair of time to voltage converters consisting of a converter for measuring the pulse shape of an exciting light and a converter for measuring the luminous shape are simultaneously activated by a start pulse so that the measurement of the pulse shape of the exciting light and the measurement of the luminous shape can be carried out in parallel in order to reduce the measurement time and to measure the luminous lifetime of the sample with a high accuracy.

2 Claims, 4 Drawing Figures

APPARATUS FOR MEASURING THE LUMINOUS LIFETIME OF A SAMPLE

BACKGROUND OF THE INVENTION

1. Field of the Invention

The present invention relates to an apparatus for measuring the luminous lifetime of a sample. More particularly, the present invention relates to an apparatus for measuring a radiation lifetime which is not as long as the pulse width of an emitted exciting light.

2. Description of the Prior Art

When the luminous lifetime of a sample is sufficiently longer than the pulse width of the emitted exciting light, only the luminous shape thereof is measured and the luminous lifetime thereof is derived from the attenuation curve of said luminous shape.

When the luminous lifetime of a sample is not as long as the pulse width of the emitted exciting light, the luminous shape thereof is influenced by the pulse width to give rise to distortions.

As a result, in the second case, it is necessary to measure not only the luminous shape of a sample but also the pulse shape of the emitted exciting light. These quantities are expressed by the true luminous shape and the convolution integral equation. If the measured luminous shape is I(t), and the pulse shape of the emitted exciting light is P(t), and the true luminous shape is G(t), then the convolution integral equation is expressed by the following formula:

$$I(t) = \int_0^t P(t')G(t-t')dt'$$

G(t) is obtained from I(t) and P(t) by a deconvolution operation to find the luminous lifetime.

In a case when the luminous lifetime of the sample is measured by conventional methods on the basis of a time correlation photon counting technique, a single photoelectron pulse can be measured for one radiation time interval and the measurement requires a long time period due to a low photometric efficiency.

An apparatus for measuring a plurality of photoelectron pulses for one radiation time interval in order to eliminate the above described defects is disclosed in Japanese Laid-Open Pat. No. 137843/1982. This apparatus, as schematically shown in FIG. 1, consists of a light source 1 which emits a pulse of light, an optical detector 3 which receives light radiated from a sample 2 to which the pulse of light is supplied and which emits a photoelectron pulse, a start pulse generating means 4 (usually comprising a photomultiplier tube 5 and a waveshape regulating circuit 6) which emits a start pulse when the pulse of light is radiated from the light source 1, a plurality of time-voltage converters 7 (hereinafter referred to as TACs) which are activated by a start pulse emitted from the start pulse generating means 4 and which are stopped in turn by a plurality of photoelectron pulses which are used as stop pulses and which are emitted from the optical detector 3 through a pulse shape regulating circuit 6', a multiplexer 8 which selectively outputs signals from the TACs 7, and a memory circuit means 9 which stores output signals from the multiplexer 8.

When the luminous lifetime of a sample is measured by a deconvolution operation in a conventional apparatus, the sample 2 must be replaced by a scattering body at those times other than the time when the luminous shape I(t) of the sample 2 is being measured so as to measure the pulse shape P(t) of the emitted exciting light. Even though a multi-channel TAC is generally used in order to shorten the measurement time, the resolution power of this apparatus for pulses is limited. In a case when a plurality of photoelectron pulses are generated within this limit, an individual photoelectron pulse cannot be distinguished from another pulse. That is to say, the effect of a multi-channel TAC cannot be completely exploited. Consequently, the defect that the measurement requires a long time period still remains. Accordingly, if a sample has a comparatively short lifetime, even though the pulse-exciting light frequency is about 20 KHz, it frequently takes one hour to measure the pulse shape of the exciting light and one or more hours to measure the luminous shape, that is to say, two or more hours in all. In some cases, when a lower frequency pulse laser is used, it takes 10 or more hours to measure only the pulse shape of the exciting light. In addition, in some cases when the measurement requires such a long time period, the pulse shape of the exciting light may change. Accordingly, in a case when P(t) and I(t) are measured at different times, the measured P(t) may be different from P(t) at the time when I(t) was measured. As a result, even though the luminous lifetime is obtained by a deconvolution operation, a large error is produced.

SUMMARY OF THE INVENTION

It is an object of the present invention to eliminate the above described defects by developing an apparatus which is capable of simultaneously measuring the pulse shape of an emitted exciting light and the luminous shape.

An apparatus for measuring the luminous lifetime of a sample according to the present invention comprises a light source for generating pulses of light, a means for generating a start pulse used as the time standard for said pulses of light, a means for dividing each of said pulses of light emitted from said light source into two parts, an optical detector for receiving one of the divided light pulses and for emitting photoelectron pulses so as to thereby measure the pulse shape of the emitted exciting light, an optical detector for receiving the radiation from a sample to which the second of the two divided light pulses was supplied and for emitting photoelectron pulses so as to thereby measure the luminous shape thereof, and a TAC for measuring the pulse shape of the exciting light as well as a TAC for measuring the luminous shape which are separately connected to said optical detectors, said TACs being simultaneously activated by said start pulse, said TAC for measuring the pulse shape of the exciting light using a photoelectron pulse from said optical detector as a stop pulse for measuring the pulse shape of the exciting light while said TAC for measuring the luminous shape uses a photoelectron pulse from said optical detector as a stop pulse for measuring the luminous shape so as to thereby output a voltage which is proportional to the time from the start of the action to the reception of a photoelectron pulse, a histogram consisting of the pulse shape of the exciting light and the luminous shape being formed from the outputs of both TACs by means of an analog-to-digital converter which acts as a multi-channel wave height analyzer, and further comprising a computer, wherein the luminous lifetime is calculated by a deconvolution operation based on the waveshape of said histogram.

DESCRIPTION OF THE PREFERRED EMBODIMENT

Figure 1:
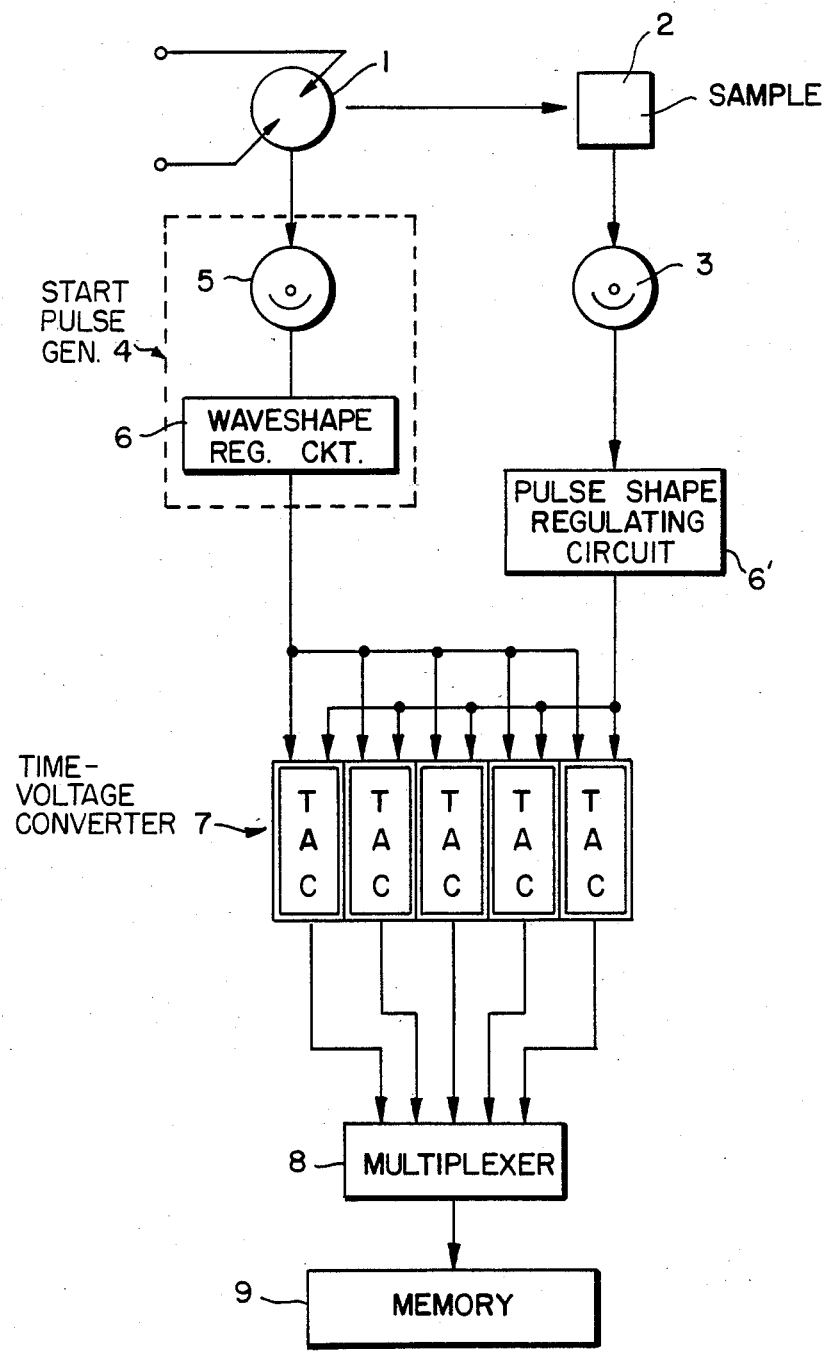
FIG. 1 is a block diagram showing a conventional apparatus for measuring the luminous lifetime of a sample.
Figure 2:
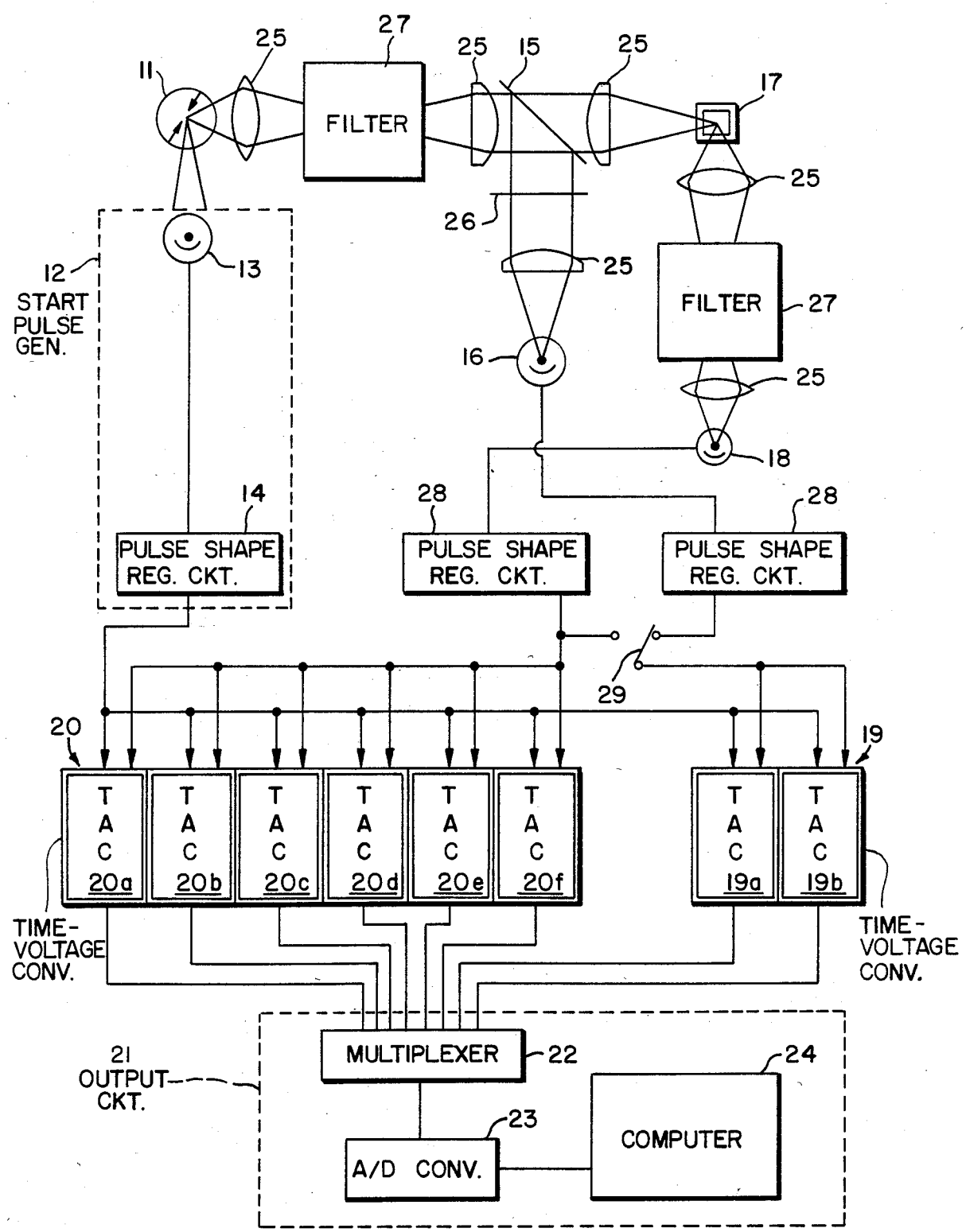
FIG. 2 is a block diagram showing one embodiment of the present invention.

The preferred embodiment of the present invention will be described below with reference to the drawings. Referring now to FIG. 2 showing the preferred embodiment of the present invention, element 11 denotes a light source for generating pulses of light; element 12 denotes a means for generating a start pulse used as the time standard for the light pulses, and comprising, for example, a photo multiplier tube 13 and a pulse shape regulating circuit 14. Element 15 denotes a means for dividing each of the pulses of light emitted from the light source 11 into two parts and comprising, for example, a beam splitter; element 16 denotes an optical detector for receiving one of the light pulses divided by the dividing means 15 and for emitting a photoelectron pulse so as to thereby measure the pulse shape of the emitted exciting light and comprising, for example, a photomultiplier tube; element 17 denotes a sample to which another of the light pulses which have been divided by the dividing means 15 has been supplied; element 18 denotes an optical detector for receiving a light emitted from the sample 17 and for emitting a photoelectron pulse so as to thereby measure the luminous shape and comprising, for example, a photomultiplier tube; and elements 19 and 20 are TAC units which are separately connected to the respective optical detectors 16 and 18. The TAC connected to the optical detector 16 is called the TAC for measuring the pulse shape of the exciting light while the TAC connected to the optical detector 18 is called the TAC for measuring the luminous shape. A capacitor within each of the TACs 19 and 20 simultaneously begins to be charged by a constant current upon receipt of a start pulse and the charging is stopped when a photoelectron pulse is input. Consequently, a voltage is output which is proportional to the time from the start of operation of a start pulse to an input of a photoelectron pulse. In addition, as is obvious from the above, a single TAC can count a single photoelectron pulse. Accordingly, both TAC 19 and TAC 20 are generally constructed as multi-channel units so that a plurality of photoelectron pulses emitted from an optical detector during one radiation event can be counted one by one by means of the TAC for each channel. Such a multi-channel construction is disclosed, for example, in Japanese Laid-Open Pat. No. 137843/1982 and is well known.

In the preferred embodiment shown in FIG. 2, TAC 19 comprises 2 channels 19$a$ and 19$b$ while TAC 20 comprises 6 channels 20$a$, - - - , 20$f$. Element 21 denotes a circuit means for outputting the output signals from both TAC 19 and TAC 20 so as to form a histogram consisting of the pulse shape of the emitted exciting light and the luminous shape and further carrying out a deconvolution operation on the basis of the histogram; the circuit means 21 may consist of a multiplexer 22, an analog-to-digital converter 23 and a computer 24.

Figure 3:
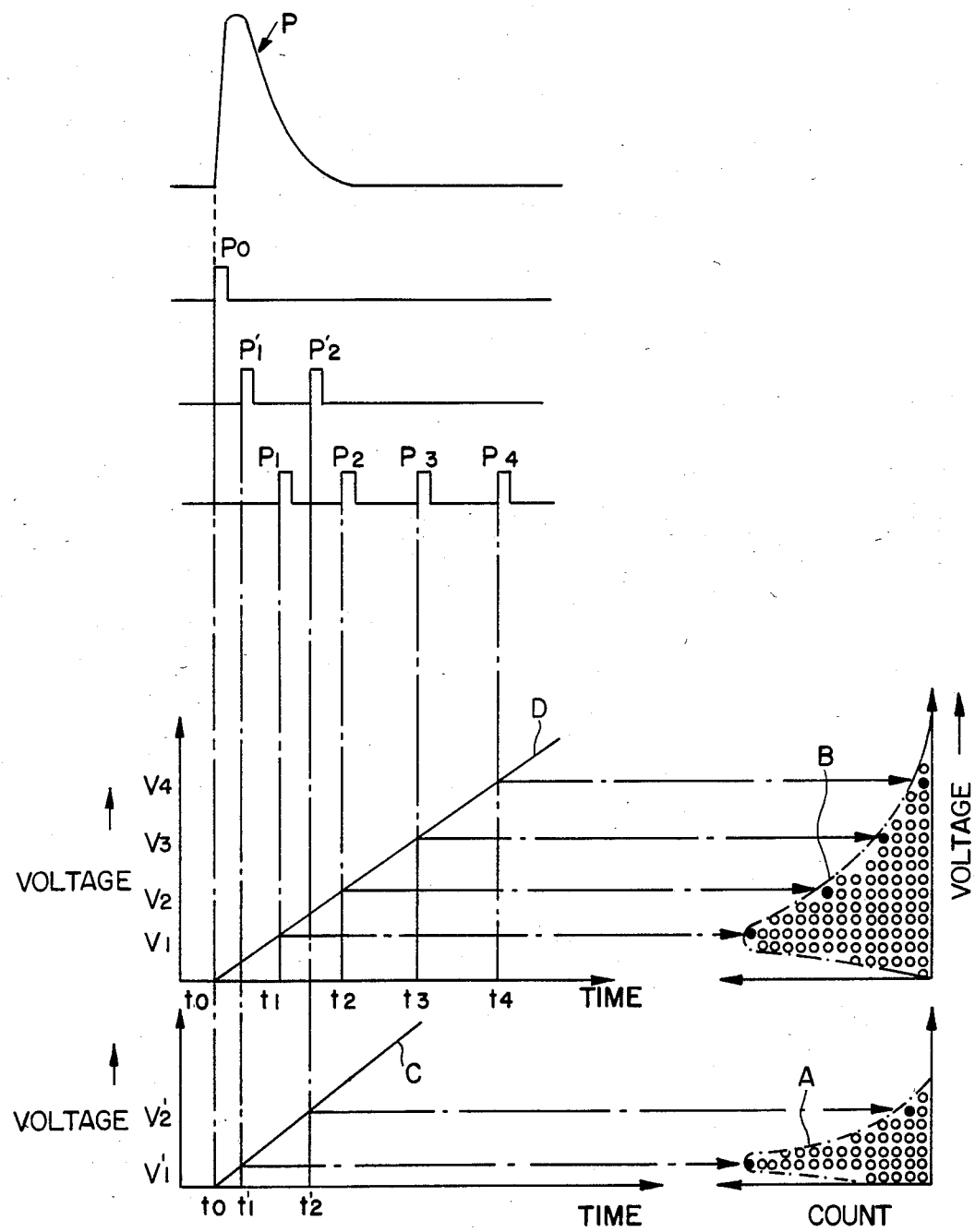
FIG. 3 is a diagram showing the operation of measurement by the apparatus shown in FIG. 2.

According to the above described construction, if the light source 11 emits one pulse of light P; the means for generating a start pulse 12 detects the risetime of said pulse light P so as to emit a start pulse $P_0$ in a manner as is shown in FIG. 3. TACs 19 and 20 are simultaneously activated by the pulse $P_0$. In addition, the pulse of light P is divided into two parts by the beam splitter 15. One of the divided two light pulses is supplied to the optical detector 16 for measuring the pulse shape of the exciting light while the other of the divided two light pulses is supplied to the sample 17. The optical detector 16 receives the pulse of light and emits photoelectron pulses $P'_1$ and $P'_2$ while the sample 17 is excited by the pulse of light P so as to emit light. This radiation is received by the optical detector 18 for measuring the luminous shape. As a result, photoelectron pulses $P_1, P_2 \ldots P_n$ are emitted. Each of the pulses $P'_1, P'_2, P_1, P_2 \ldots P_n$ acts on each of the TACs 19 and 20 as a stop pulse. As a result, each of the TACs 19 and 20, in particular, each of the channels of TACs 19$a$, 19$b$, 20$a$, 20$b$, ... 20$n$ outputs an analog voltage which is proportional to the time interval from the time when channels 19$a$, 19$b$, 20$a$, 20$b$ ... 20$n$ were simultaneously activated to the time when the photoelectron pulses $P'_1, P'_2, P_1, P_2 \ldots P_n$ are input. These output signals are output by the subsequent output circuit means 21.

Output signals which are output from each of the TACs 19 and 20 every time a light pulse is repeatedly emitted by the light source 11 are stored in separate memory groups of a computer acting as a wave-height analyzer. As a result, the histogram, as shown by curves A and B of FIG. 3, of the frequency of the photoelectron generation is obtained with the ordinate axis expressing voltages and the abscissa axis expressing count numbers of output signals of the same voltage. Since the voltage is equivalent to the time, the curve A of this histogram expresses the pulse shape of the emitted exciting light $P(t)$ while the curve B of the histogram expresses the luminous shape $I(t)$ which may occur in the computer 24 in the circuit means 21. The luminous lifetime is obtained from this true luminous shape $G(t)$.

Figure 4:
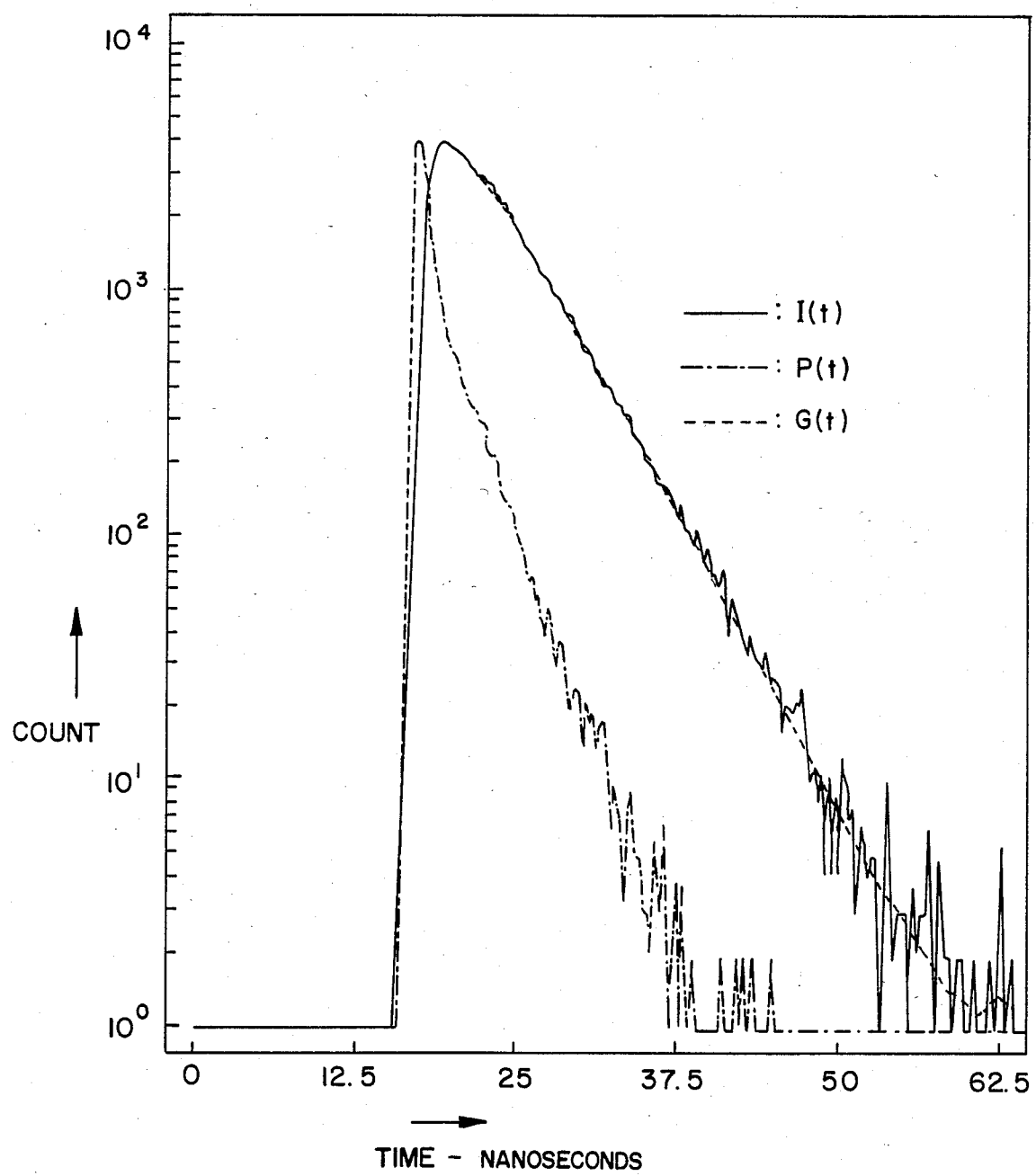
FIG. 4 is a diagram showing the data obtained by the apparatus shown in FIG. 2.

FIG. 4 shows the experimental data for the case when anthracene dissolved in solvents is used as the sample. The abscissa axis expresses time while the ordinate axis expresses count number. Furthermore, referring to FIG. 3, the curve C expresses the operational characteristics of TACs 19$a$ and 19$b$ while the curve D expresses the operational characteristics of TACs 20$a$, 20$b$, 20$c$, 20$d$, 20$e$, and 20$f$. Points $t'_1, t'_2, t_1, t_2$ denote the times until photoelectron pulses $P_{1'}, P_{2'}, P_1, P_2$ are input, and $V_1, V_2$ - - - express the voltages equivalent to each of the above described times. The operational characteristic of each TAC is shown one above the other with start pulses being used as the same time standard. In addition, referring now to FIG. 2, element 25 denotes a condenser lens, element 26 denotes a light-reducing means; element 27 denotes a filter or spectrometer; element 28 denotes a pulse shape regulating circuit, and element 29 denotes a change-over switch. The TAC 19 is connected in parallel to the TAC 20 by changing-over the change-over switch 29 whereby the luminous shape $I(t)$ can be measured by a TAC having 8 channels in all. However, during this period of time, the pulse shape of the exciting light $P(t)$ cannot be simultaneously measured. Accordingly, radiation having a sufficiently long lifetime in comparison to the pulse-width of the exciting light can be efficiently measured by changing-over the change-over switch 29 so as to make use of the characteristics of a multi-channel TAC. Thus, an apparatus according to the present invention can be applied to extensive kinds of samples.

An apparatus for measuring the luminous lifetime of a sample according to the present invention exhibits the following effects due to the above described construction:

(1) The measurement time can be reduced by half since the luminous shape I(t) and the pulse shape of the exciting light P(t) can be simultaneously measured. In particular, the photometric efficiency can be improved along with a significant reduction of the measurement time.

(2) Since the measurement time is reduced and the pulse shape of the exciting light P(t) and the luminous shape I(t) are simultaneously influenced by the effect of the changes in the pulse shape of the exciting light, not only are the effects of ageing of the exciting light reduced but also the luminous lifetime can be obtained with high accuracy by a deconvolution technique.

(3) Since an apparatus according to the present invention comprises apparatus disclosed in Japanese Laid-Open Patent No. 137,843/1982 to which the beam splitter 15, the optical detector for measuring the pulse shape of the exciting light and the TAC 19 have been added, the apparatus disclosed in Japanese Laid-Open Patent No. 137,843/1982 can be easily improved so as to construct an apparatus according to the present invention by adding these parts thereto. Accordingly, an apparatus according to the present invention can utilize most of the parts of a conventional apparatus whereby it is practically used with ease. Furthermore, in this time, if the TAC comprises a plurality of channels in the conventional apparatus, some of a plurality of channels can be used as the TAC for measuring the pulse chape of the exciting light. Thus, the present invention can be effected by adding a beam splitter and an optical detector to the conventional apparatus and further correcting the TAC control signals which come from a computer.

(4) On the other hand, an apparatus according to the present invention uses a pair of TACs consisting of a TAC for measuring the pulse shape of the exciting light and a TAC for measuring the luminous shape. As a result, in a case when the luminous lifetime is sufficiently long in comparison with the pulse-width of the exciting light to be measured, not only can the photometric efficiency be significantly raised but also the measurement can be carried out in such a manner corresponding to the sample by constructing the system so that both TACs may be connected to each other in parallel by changing-over the change-over switch, as shown in the preferred embodiment, and effectively using all of the TACs, which are contained in an apparatus, as a series.

What is claimed is:

1. An apparatus for measuring the luminous lifetime of a sample comprising:
   a light source for generating light pulses;
   a means for generating a start pulse used as a time standard for said light pulses;
   a means for dividing each of said light pulses generated by said light source into two parts;
   a first optical detector for receiving one of said two divided light pulses so as to emit a photoelectron pulse so as to thereby measure the pulse shape of an emitted exciting light pulse;
   a second optical detector for receiving radiation emitted from said sample to which the other of said two divided light pulses was applied so as to emit a photoelectron pulse so as to thereby measure a luminous shape of said sample;
   and a time to voltage converter for measuring the pulse shape of said emitted exciting light pulse and another time to voltage converter for measuring said luminous shape, said two converters being separately respectively connected to said two optical detectors, wherein said two converters are simultaneously activated by said start pulse, said converter for measuring said pulse shape of said exciting light using a photoelectron pulse from said first optical detector as a stop pulse for measuring the pulse shape of said exciting light while said converter for measuring said luminous shape uses a photoelectron pulse from said second optical detector as a stop pulse for measuring said luminous shape, so as to output a voltage which is proportional to the time from the start of said start pulse to the reception of its respective photoelectron pulse, whereby said luminous lifetime may be calculated by a deconvolution operation of a histogram obtained on the basis of output voltages of both of said converters; and
   wherein, said converter for measuring said pulse shape of said exciting light and said converter for measuring said luminous shape are connected in parallel by changing-over a change-over switch which is connected thereto.

2. An apparatus for measuring the luminous lifetime of a sample as set forth in claim 1, wherein both said converter for measuring said pulse shape of said exciting light and said converter for measuring said luminous shape comprise multi-channel converters.

* * * * *